United States Patent
Shimizu et al.

(10) Patent No.: US 9,723,983 B2
(45) Date of Patent: Aug. 8, 2017

(54) CORNEAL ENDOTHELIAL CELL PHOTOGRAPHING APPARATUS

(71) Applicant: NIDEK CO., LTD., Gamagori-shi, Aichi (JP)

(72) Inventors: Kazunari Shimizu, Toyokawa-shi (JP); Kenji Nakamura, Toyohashi (JP); Yusuke Sakashita, Okazaki (JP)

(73) Assignee: NIDEK CO., LTD., Gamagori (JP)

( * ) Notice: Subject to any disclaimer, the term of this patent is extended or adjusted under 35 U.S.C. 154(b) by 0 days.

(21) Appl. No.: 14/714,988

(22) Filed: May 18, 2015

(65) Prior Publication Data
US 2015/0327763 A1    Nov. 19, 2015

(30) Foreign Application Priority Data

May 19, 2014 (JP) .................... 2014-102956

(51) Int. Cl.
| | |
|---|---|
| A61B 3/14 | (2006.01) |
| A61B 3/00 | (2006.01) |
| A61B 3/10 | (2006.01) |
| A61B 3/02 | (2006.01) |
| A61B 3/15 | (2006.01) |

(52) U.S. Cl.
CPC .............. *A61B 3/14* (2013.01); *A61B 3/1005* (2013.01); *A61B 3/145* (2013.01); *A61B 3/152* (2013.01)

(58) Field of Classification Search
CPC A61B 3/14; A61B 3/103; A61B 3/113; A61B 3/1208; A61B 3/1225; A61B 3/024; A61B 3/032; A61B 3/1015
USPC ........... 351/206, 200, 205, 209–211, 218, 351/221–223, 246
See application file for complete search history.

(56) References Cited

U.S. PATENT DOCUMENTS 6,155,683 A * 12/2000 Hanaki ............... A61B 3/145
                                                      351/206
2008/0055544 A1 * 3/2008 Nishio ............... A61B 3/145
                                                      351/208

FOREIGN PATENT DOCUMENTS

JP   2011-245184 A   12/2011

* cited by examiner

*Primary Examiner* — Dawayne A Pinkney
(74) *Attorney, Agent, or Firm* — Oliff PLC

(57) ABSTRACT

A corneal endothelial cell photographing apparatus for photographing endothelial cells of a patient eye's cornea, includes: a cornea photographing optical system including an imaging device and configured to project light toward the cornea and photograph the corneal endothelial cells through the imaging device; a light projecting optical system to project detection light in a first oblique direction to the cornea to detect a focus state of the cornea photographing optical system relative to the cornea; a detecting optical system including a detector with arranged pixels and configured to receive, in a second oblique direction opposite to the first oblique direction, corneal reflection light resulting from the detection light and including reflection light from the corneal endothelium through the detector, and detect an intensity distribution of the corneal reflection light in a depth direction; and a controller to cause a monitor to display the intensity distribution output from the detector.

15 Claims, 9 Drawing Sheets

CORNEAL ENDOTHELIAL CELL PHOTOGRAPHING APPARATUS

CROSS-REFERENCE TO RELATED APPLICATIONS

This application is based upon and claims the benefit of priority from the prior Japanese Patent Applications No. 2014-102956 filed on May 19, 2014, the entire contents of which are incorporated herein by reference.

BACKGROUND

The present disclosure relates to a corneal endothelial cell photographing apparatus for photographing corneal endothelial cells of an examinee's eye.

There is known a corneal endothelial cell photographing apparatus arranged to irradiate illumination light toward a cornea of an examinee's eye and receive reflection light from endothelial cells of the cornea, thus photographing an endothelial cell image (see Patent Document 1).

The apparatus of the above type performs positioning of a main unit of the apparatus with respect to an examinee's eye so as to focus on a portion close to a corneal epithelium and then further moves the position of the apparatus with respect to the examinee's eye to adjust a focus point (diopter), and obtains or captures a corneal epithelial image at the adjusted focus position.

RELATED ART DOCUMENTS

Patent Documents

Patent Document 1: JP-A-2011-245184

SUMMARY

Meanwhile, if an examinee's eye has a distorted corneal shape or includes opacity or the like between epithelium and endothelium depending on a disease or other reasons, it may be difficult to appropriately adjust focus with respect to the corneal endothelium.

The present disclosure has been made under the above problems of the conventional arts and has a purpose to provide a corneal endothelial cell photographing apparatus capable of easily obtaining an endothelial cell image with a focus adjusted well.

One aspect of the present disclosure provides a corneal endothelial cell photographing apparatus for photographing endothelial cells of a cornea of an examinee's eye, comprising: a cornea photographing optical system including an imaging device and being configured to project light from a photographing light source toward the cornea of the examinee's eye and photograph the corneal endothelial cells of the examinee's eye through the imaging device; a light projecting optical system configured to project detection light in a first oblique direction to the cornea of the examinee's eye to detect a focus state of the cornea photographing optical system with respect to the cornea of the examinee's eye; a detecting optical system including a detector in which a plurality of pixels are arranged, the detecting optical system being configured to receive, in a second oblique direction opposite to the first oblique direction, corneal reflection light resulting from the detection light and including reflection light from the corneal endothelium through the detector, and detect an intensity distribution of the corneal reflection light in a depth direction; and a controller configured to cause a monitor to display the intensity distribution output from the detector.

DETAILED DESCRIPTION OF THE EXEMPLARY EMBODIMENTS

Figure 1:
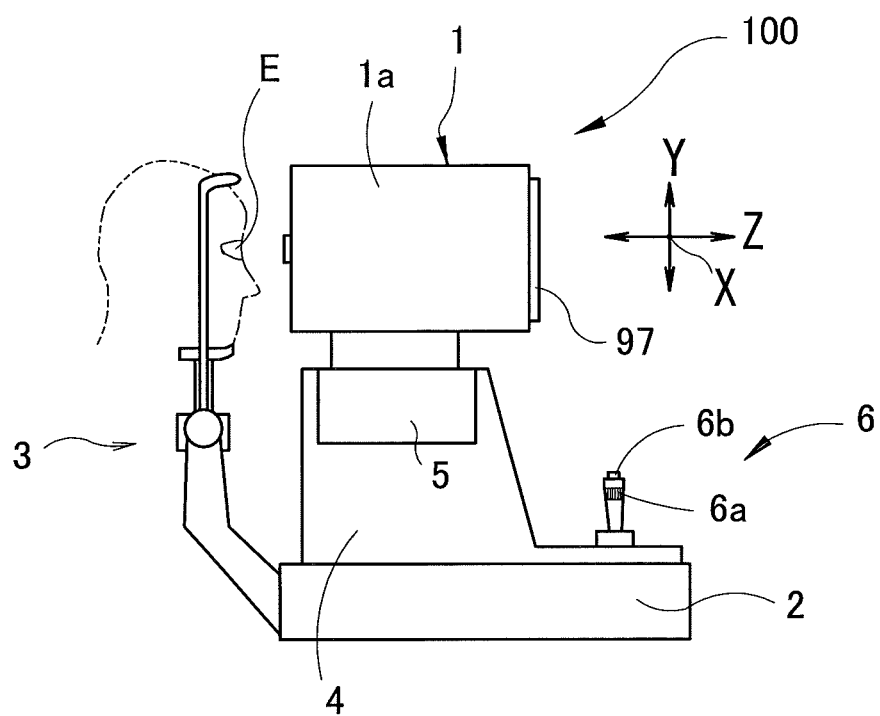
FIG. 1 is an external side configuration view of a corneal endothelial cell photographing apparatus in a first embodiment.

A typical embodiment of the present disclosure will be explained, referring to accompanying drawings. Referring to FIG. 1, firstly, an external configuration of a corneal endothelial cell photographing apparatus 100 (hereinafter, simply referred to as a "photographing apparatus 100") in the present embodiment will be explained. The following explanation is given on the assumption that an X direction in FIG. 1 is a right-and-left (lateral) direction, a Y direction is an up-and-down (vertical) direction, and a Z direction is a back-and-forth (longitudinal) direction.

The photographing apparatus 100 is an apparatus for photographing an image of a corneal portion of an examinee's eye E. The photographing apparatus 100 includes a photographing part 1 (a main unit), a table 2, a head support unit 3, and a movable unit 4. This apparatus 100 is a so-called stationary apparatus. Optical systems in the photographing apparatus 100 are accommodated in a housing 1*a* of the photographing part 1.

The movable unit 4 is movable on the table 2 by a sliding mechanism not shown. In the movable unit 4, an XYZ actuator (drive part) 5 is provided. The photographing part 1 is moved by the XYZ actuator 5 in the right-and-left direction (X direction), the up-and-down direction (Y direction), and the back-and-forth direction (Z direction) with respect to the eye E. The movable unit 4 is moved in the X-Z directions on the table 2 by operation of a joystick 6. When a rotary knob 6*a* is rotated by an examiner, the photographing part 1 is moved in the Y direction by Y-drive of the XYZ actuator 5. At the top of the joystick 6, a start switch 6*b* is provided. A monitor 97 is placed on an examiner side of the housing 1a of the photographing part 1. In the present embodiment, the photographing part 1 is moved relative to the examinee's eye E by a sliding mechanism not shown or the XYZ actuator 5.

The configuration of moving the photographing part 1 may be arranged to move the photographing part 1 by drive of a motor of the actuator 5 with respect to right and left eyes without providing any mechanical sliding mechanism. The apparatus 100 may also be provided with a touch panel or touchscreen serving as a manual operation member such as the joystick 6.

In the present embodiment, the housing 1a is provided with the monitor 97 on a surface opposite a side surface that will face to an examinee. However, this monitor 97 may be placed in another position of the housing 1a or may be provided as a device separate from the photographing apparatus 100.

Figure 2:
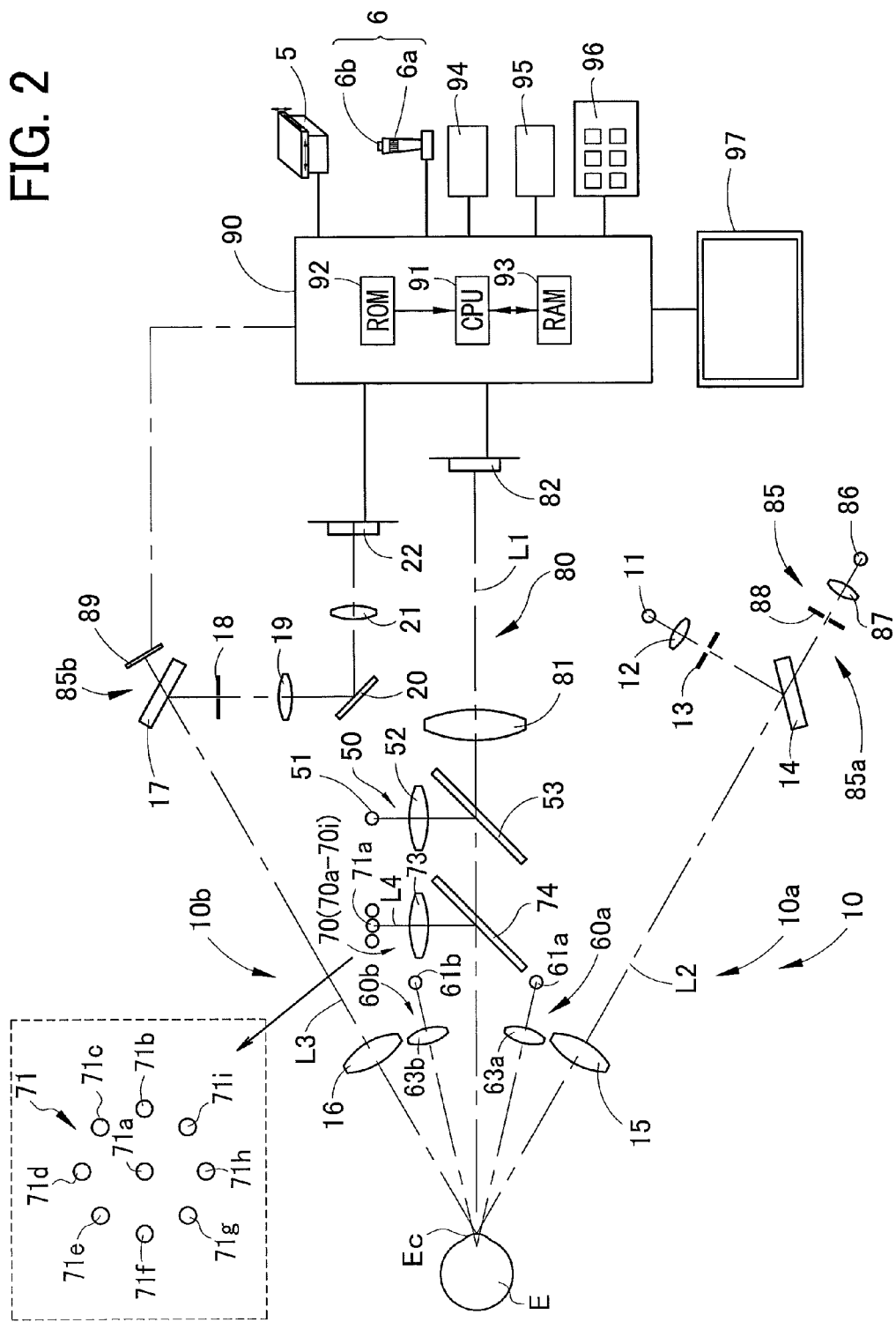
FIG. 2 is a schematic configuration view showing one example of optical arrangement of optical systems accommodated in a housing of a photographing part seen from above and a configuration of a control system.

Next, optical systems and a control system of the photographing apparatus 100 will be explained, referring to FIG. 2. The optical arrangement shown in FIG. 2 is the layout of the optical systems accommodated in the photographing part 1 seen from above.

Figure 3:
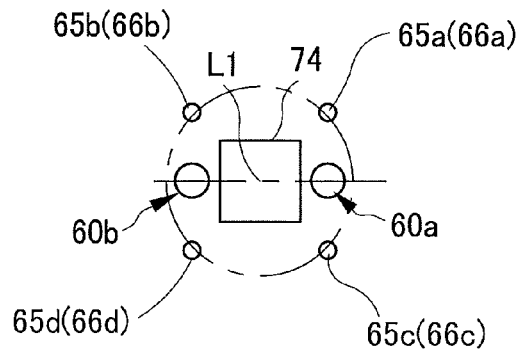
FIG. 3 is a diagram of first and second projection optical systems seen from an examinee's side.

The photographing apparatus 100 mainly includes a cornea photographing optical system 10 and a Z alignment detecting optical system 85. The photographing apparatus 100 in the present embodiment includes a front projection optical system 50, first projection optical systems 60a and 60b, second projection optical systems 65a to 65d (see FIG. 3), a fixation optical system 70 (70a to 70i), and an anterior segment observing optical system 80.

The cornea photographing optical system 10 includes an illumination optical system 10a and a light receiving optical system 10b. The cornea photographing optical system 10 is configured to project the light from an illumination light source 11 (a first light source) to a cornea Ec of the examinee's eye E through the illumination optical system 10a. The cornea photographing optical system 10 is also configured to receive, through an imaging device 22, reflection light irradiated from the illumination light source 11 and reflected by the cornea Ec. The photographing apparatus 100 photographs a corneal portion of the eye E in a non-contact manner by use of the cornea photographing optical system 10.

The optical axes of the illumination optical system 10a and the light receiving optical system 10b intersect each other, for example, on the examinee's eye E. It is advantageous to place those optical systems 10a and 10b symmetrically with respect to a certain center axis. In the present embodiment, an optical axis L2 of the illumination optical system 10a and an optical axis L3 of the light receiving optical system 10b are bilaterally symmetric with respect to the optical axis L1.

The illumination optical system 10a in the present embodiment includes an illumination light source 11, a condensing lens 12, a slit plate 13, a dichroic mirror 14, and a light projecting lens 15. The illumination light source 11 emits illumination light to be used in photographing a corneal portion. In the present embodiment, the illumination light source 11 emits visible light. As the illumination light source, for example, a visible LED, a flash lamp, and others may be employed. The dichroic mirror 14 reflects visible light, while transmits infrared light. The slit plate 13 and the cornea Ec are placed in almost conjugate positions with respect to the light projecting lens 15. The light emitted from the illumination light source 11 is condensed by the condensing lens 12 and passes through a slit formed in the slit plate 13. The slit light passing through the slit plate 13 is reflected by the dichroic mirror 14 and converged by the light projecting lens 15 and irradiated to the cornea Ec.

The light receiving optical system 10b receives reflection light from the cornea Ec including endothelial cells through the imaging device 22. This optical system 10b in the present embodiment includes an objective lens 16, a dichroic mirror 17, a mask 18, a first image-forming lens 19, a total reflection mirror 20, a second image-forming lens 21, and a two-dimensional imaging device 22 (hereinafter, simply referred to as an "imaging device 22"). The dichroic mirror 17 reflects visible light, while transmits infrared light. The mask 18 is placed in an almost conjugate position with the cornea Ec. The first image-forming lens 19 and the second image-forming lens 21 constitute an image-forming optical system for forming an endothelial cell image on the imaging device 22. The imaging device 22 is used to photograph endothelial cells. The imaging device 22 is placed in an almost conjugate position with the cornea Ec. As the imaging device 22, for example, there may be employed a two-dimensional CCD image sensor (Charge Coupled Device image sensor), a two-dimensional CMOS (Complementary Metal Oxide Semiconductor image sensor), and others.

The light delivered from the illumination optical system 10a to the cornea Ec is reflected by the cornea Ec toward an optical axis L3 direction (an oblique direction). Thereafter, the light forms an image once on the mask 18 through the objective lens 16 and the dichroic mirror 17. The mask 18 blocks the light that may become noise when an endothelial cell image is obtained. The light passing through the mask 18 forms an image on the imaging device 22 via the first image-forming lens 19, the total reflection mirror 20, and the second image-forming lens 21. Thus, a highly magnified (zoomed-in) endothelial cell image is obtained.

The front projection optical system 50 projects an alignment target for alignment in X- and Y-directions (XY alignment) from front toward the cornea Ec. The front projection optical system 50 includes an infrared light source 51, a light projecting lens 52, and a half mirror 53. When the infrared light source 51 lights up, the optical system 50 projects infrared light for XY alignment detection to the cornea Ec from the optical axis L1 direction.

The first projection optical systems 60a and 60b and the second projection optical systems 65a to 65d project alignment targets for XYZ analysis. In the photographing apparatus 100, rough alignment is performed by utilizing the alignment targets projected from the first projection optical system 60a and 60b and the second photographing optical system 65a to 65d.

The first projection optical systems 60a and 60b project infinite alignment targets toward the cornea Ec from oblique directions. The first projection optical systems 60a and 60b are arranged respectively at predetermined angles with respect to the optical axis L1. The first projection optical systems 60a and 60b respectively include infrared light sources 61a and 61b and collimator lenses 63a and 63b, and are arranged symmetric with respect to the optical axis L1 and configured to project infinite targets to the eye E (see FIG. 3). The first projection optical systems 60a and 60b are located on approximately the same meridian as the horizontal direction passing the optical axis L1 (see FIG. 3).

Figure 4A:
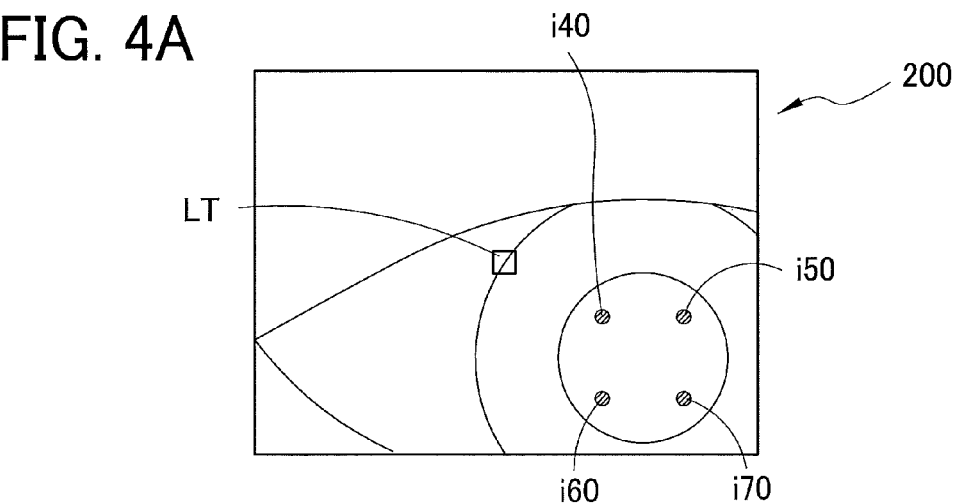
FIGS. 4A and 4B are diagrams showing one example of an anterior segment observation screen in photographing an endothelium of a corneal central portion, FIG. 4A showing a misaligned state and FIG. 4B showing a properly aligned state.

The lights emitted from the light sources 61a and 61b are collimated respectively by collimator lenses 63a and 63b, and then projected onto the cornea Ec, forming target images i20 and i30 (see FIG. 4).

The second projection optical systems 65a to 65d respectively project finite alignment targets toward the cornea Ec from a plurality of oblique directions. The second projection optical systems 65a to 65d are each placed at a slant with respect to the optical axis L1. The second projection optical systems 65a to 65d respectively include infrared light sources 66a to 66d and are arranged symmetric with respect to the optical axis L1 to project the finite targets to the eye E. The second projection optical systems 65a and 65b are located above the optical axis L1 and at the same level as each other in the Y direction. The second projection optical systems 65c and 65d are located below the optical axis L1 and at the same level as each other in the Y direction. The second projection optical systems 65a and 65b and the second projection optical systems 65c and 65d are placed vertically symmetric with respect to the optical axis L1.

Herein, the lights from the light sources 66a and 66b are irradiated from upper oblique directions toward an upper part of the cornea Ec, forming target images i40 and i50 that are virtual images of the light sources 66a and 66b. Further, the lights from the light sources 66c and 66d are irradiated from lower oblique directions toward a lower part of the cornea Ec, forming target images i60 and i70 which are virtual images of the light sources 66c and 66d (see FIGS. 4A and 4B).

Figure 4B:
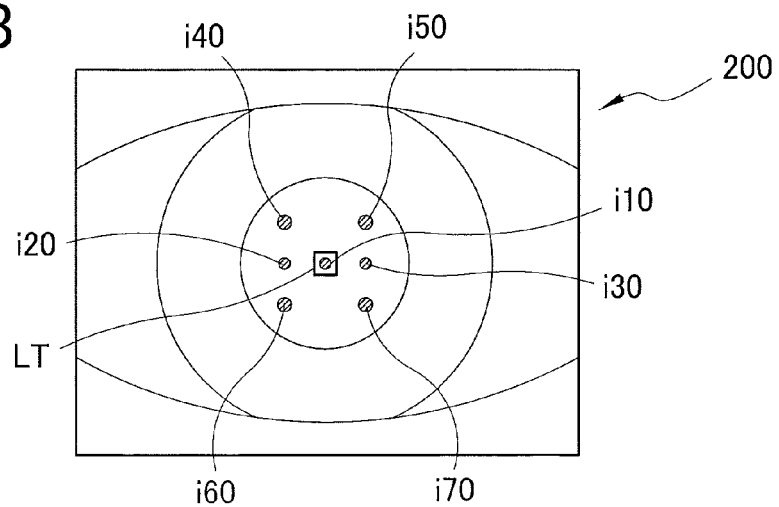

According to the above-described target projection optical system, the target image i10 is formed at a corneal apex of the eye E (see FIG. 4B). The target images i20 and i30 by the first projection optical systems 60a and 60b are formed in the same horizontal positions as the target image i10 and symmetric with respect to the target image i10. Further, the target images i40 and i50 by the second projection optical systems 65a and 65b are formed in positions above the target image i10 and symmetric with respect to the target image i10. The target images i60 and i70 by the second projection optical systems 65c and 65d are formed in positions below the target image i10 and symmetric with respect to the i10.

The photographing apparatus 100 includes a plurality of fixation optical systems (e.g., a fixation optical system 70 in FIG. 2). The fixation optical system 70 has a plurality of fixation lamps 71 (visible light sources (fixation light sources) 71a to 71i) on a plane perpendicular to the optical axis, and lighting positions are changed over to change a visual line direction of an examinee's eye E.

The fixation optical system 70 (70a to 70i) projects fixation targets from the inside of the housing 1a to the eye E. Each of the fixation optical systems 70a to 70i includes one of visible light sources (fixation lamps) 71a to 71i, a light projecting lens 73, and a dichroic mirror 74. The visible light sources (fixation lamps) 71a to 71i are arranged at different positions in a direction perpendicular to the optical axis L4. The dichroic mirror 74 reflects visible light, while transmits infrared light. The visible lights emitted from the light sources 71a to 71i are converted into parallel light flux by the light projecting lens 73, and then reflected by the dichroic mirror 74. Thus, a fixation target is projected onto a fundus of the eye E. For example, the visible light source 71a is arranged near the optical axis L4 and used to guide the eye E to a front direction. The visible light sources 71b to 71i are lighted on when an endothelium image of a central portion of the cornea Ec is to be obtained. The plurality of visible light sources 71b to 71i are arranged on the circumference centered at the optical axis L4. FIG. 2 shows an example that the light sources 71b to 71i are arranged at angular intervals of 45°, that is, at each position of 0°, 45°, 90°, 135°, 180°, 225°, 270°, and 315°, when seen from an examinee's side. The visible light sources 71b to 71i are used to guide the direction of the visual line of the eye E to a circumferential direction to obtain an endothelium image around the corneal center portion. Moreover, an external fixation optical system may be further provided on the side surface of the housing 1a on the examinee's side, even though the details and figure thereof are omitted. The present embodiment shows the case of using the optical system configured such that the plurality of fixation lamps placed at different positions are selectively lighted, thereby changing the direction to guide the visual line. The present disclosure is however not limited thereto. As an alternative, the present disclosure may include a configuration of moving a single fixation lamp in a direction perpendicular to the optical axis and changing the direction to guide the visual line of the examinee's eye E. As another alternative, a fixation optical system may include a display panel such as a liquid crystal display and an organic EL (electroluminescence) and control an emission position to change the direction to guide the visual line of the examinee's eye E.

The anterior segment observing optical system 80 is used for observation and photographing of an anterior segment image from front. This optical system 80 includes an objective lens 81 and a two-dimensional imaging device 82 (hereinafter, simply referred to as an "imaging device 82"). The imaging device 82 photographs an anterior segment image and an alignment target. Alignment in the X- and Y-directions and rough alignment in the Z direction are performed based on the alignment target images photographed by the imaging device 82. As the imaging device 82, for example, a two-dimensional CCD image sensor, a two-dimensional CMOS, and others may be employed. As the light source to be used for photographing the anterior segment, an anterior segment illumination light source not shown is used.

In the present embodiment, the Z alignment detecting optical system 85 is utilized for accurate alignment in the Z direction. This Z alignment detecting optical system 85 includes a light projecting optical system 85a and a detecting optical system 85b. In the present embodiment, the optical axis L2 of the light projecting optical system 85a and the optical axis L3 of the detecting optical system 85b are arranged in bilaterally symmetric positions with respect to the optical axis L1. The Z alignment detecting optical system 85 is configured to project the light (i.e., detection light) in a first oblique direction to the cornea Ec to detect a focus state of the cornea photographing optical system 10 with respect to the cornea Ec of the eye E. On the other hand, the detecting optical system 85b is provided with a detector 89 in which a plurality of pixels are arranged. The detector 89 receives reflection light projected from the light projecting optical system 85a and reflected by the cornea Ec. The detecting optical system 85b receives, in a second oblique direction opposite to the first oblique direction, corneal reflection light resulting from the detection light projected from the light projecting optical system 85a and including reflection light from the corneal endothelium, and thus detects an intensity distribution of the corneal reflection light in a depth direction.

The light projecting optical system 85a in the present embodiment includes an illumination light source 86, a condensing lens 87, a pinhole plate 88, and the lens 15. The pinhole plate 88 is placed in an almost conjugate position with the cornea Ec. The detecting optical system 85b in the present embodiment includes the lens 16 and the detector 89. As the detector 89, for example, a one-dimensional light receiving element (a line sensor) may be used. The detector 89 and the cornea Ec are located in almost conjugate positions. Infrared light emitted from the light source 86 illuminates the pinhole plate 88 via the condensing lens 87.

The light passing through an aperture of the pinhole plate 88 is projected onto the cornea Ec via the lens 15. The light is then reflected by the cornea Ec toward the optical axis L3. Thereafter, the corneal reflection light is received by the detector 89 via the lens 16 and the dichroic mirror 17. The detector 89 outputs a signal representing the intensity distribution of corneal reflection light in the depth direction to a controller 90.

The signal output from the detector 89 is utilized to detect the alignment state in the Z direction. Herein, the received position of the detection light on the detector 89 changes according to the positional relationship between the photographing part 1 and the examinee's eye E in the Z direction. The photographing apparatus 100 detects misalignment between the light received position of the detection light and an alignment proper position to detect an amount of misalignment in the Z direction.

A schematic configuration of the control system of the photographing apparatus 100 will be explained below.

In the photographing apparatus 100, the controller 90 controls each part of the apparatus 100. The controller 90 is connected to the actuator 5, the joystick 6, various light sources 11, 71, 51, 61, and 86, the imaging devices 22 and 82, the detector 89, the HDD 94, the image processing IC 95, an operation input unit (a user interface) 96, and the monitor 97. The monitor 97 may employ a touch panel. In this case, the monitor 97 also serves as a part of the operation input unit 96.

The controller 90 includes a CPU 91, a ROM 92, and a RAM 93. The CPU 91 is a processing unit for executing various processings in the photographing apparatus 100. The ROM 92 is a nonvolatile storage unit that stores various control programs and fixed data. The RAM 93 is used as a rewritable volatile storage unit, but is not limited thereto. The RAM 93 stores temporary data when the control program is to be executed.

The HDD 94 is used as a rewritable nonvolatile storage unit, but is not limited thereto. In the present embodiment, the HDD 94 stores a program of a main processing which will be described later. An image of the examinee's eye E photographed by the photographing apparatus 100 is stored in the HDD 94.

The image processing IC 95 is used as an image processing section. The image processing IC 95 processes a signal output from the imaging device 22 to create an endothelial cell image (hereinafter, referred to as an "endothelial image"). Further, the image processing IC 95 processes a signal output from the imaging device 82 to create an anterior segment front image (hereinafter, referred to as an "anterior segment image"). For instance, when the endothelial cell image is to be observed, the image processing IC 95 sequentially creates the endothelial images and the anterior segment images. Each of the crated images is successively output to the monitor 97. Thus, on an observation-photographing screen (an endothelium observation screen) 300 of the monitor 97 (see FIG. 7), the anterior segment front image and the corneal endothelial image are displayed as an observation image (a live image). When the endothelial image is to be photographed (captured), the CPU 91 makes the HDD 94 to store the endothelial image created by the image processing IC 95.

Figure 5:
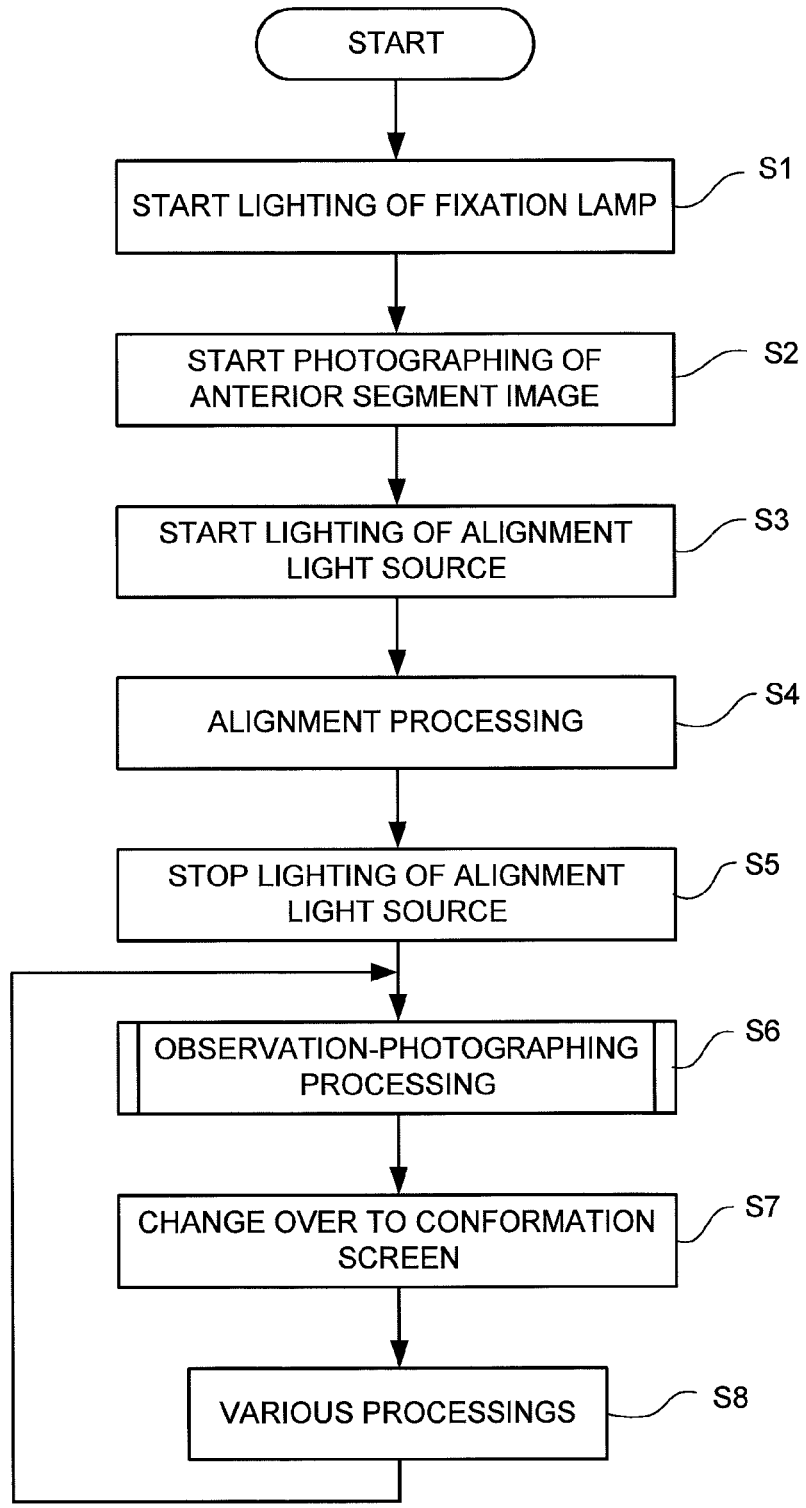
FIG. 5 is a flowchart showing main processing to be executed by a CPU.

Operations of the photographing apparatus 100 will be explained below, referring to FIG. 5. The main processing shown in FIG. 5 is executed when the power of the photographing apparatus 100 is turned on. In the main processing, firstly, the alignment of the apparatus 100 with respect to the examinee's eye E is performed by use of the anterior segment image obtained through the anterior segment observing optical system 80 (S1 to S6). The fixation lamp 71 is turned on (S1). Herein, the fixation lamp 71a near the optical axis L4 is lighted. Further, the CPU 91 starts lighting of an anterior segment observation light source not shown and starts creation of an anterior segment image (a live image) by the image processing IC 95 and output of the image to the monitor 97 (S2). Further, the CPU 91 causes the monitor 97 to display the anterior segment observation screen 200 (see FIG. 4) (S3). The anterior segment observation screen 200 is displayed when the position of the photographing part (measuring part) 1 is to be aligned with the examinee's eye E. On the anterior segment observation screen 200, an anterior segment image photographed in real time is displayed. While checking or confirming this screen 200, an examiner operates the joystick 6 to adjust the position of the photographing part 1 with respect to the examinee's eye E.

Subsequently, the light source for alignment is turned on (S3). Further, the alignment processing is executed (S4). In this alignment processing (S4), alignment of the photographing part 1 with respect to the eye E is performed. In the present embodiment, the alignment in the X- and Y-directions is carried out in two stages; rough alignment performed manually by operation of the joystick 6 and automatic alignment. While the manual alignment is being performed by operation of the joystick 6, the CPU 91 detects the target images i40, i50, i60, and i70 of the targets projected by the second projection optical systems 65a to 65d. As soon as the target images i40 to i70 get detected, the CPU 91 detects the center position of a rectangle formed by the target images i40 to i70 as a nearly corneal apex and detects a misalignment direction and/or deviation amount in the X- and Y-directions. The CPU 91 moves the photographing part 1 in the X- and Y-directions to bring the misalignment into an allowable range. When a target image i10 is detected, accordingly, the CPU 91 terminates the alignment using the target images i40 to i70 and starts alignment using the target image i10. The CPU 91 moves the photographing part 1 in the X- and Y-directions to bring the displacement amount between the target image i10 and an alignment reference point (e.g., the center of the screen 20a) into an allowable range. The alignment in the X- and Y-directions is performed in the above manner.

In the present embodiment, the alignment in the Z direction is carried out in two stages; first automatic alignment and second automatic alignment. The first automatic alignment uses a detection result of the infinite target images i20 and i30 and the finite target images i60 and i70. When the target image i10 gets detected, the infinite target images i20 and i30 are also detected. The CPU 91 compares an interval between the target images i20 and i30 and an interval between the target images i60 and i70 to determine a misalignment direction and/or deviation amount in the Z direction (first alignment detection). Further, the CPU 91 moves the photographing part 1 in the Z direction to bring the Z-direction misalignment into an allowable range (first automatic alignment). Herein, the Z-direction misalignment is determined by utilizing the characteristic that the interval between the infinite target images i20 and i30 changes little when the photographing part 1 is displaced in an operating direction, whereas the interval between the finite target images i60 and i70 changes (for the details, see JP-A-H6 (1994)-46999). It is to be noted that the target images i40 and i50 may be used instead of the target images i60 and i70.

An alignment state in the Z direction may be detected based on a distance of a target (target height) from the optical axis L1.

After completion of the first automatic alignment, the second automatic alignment is performed. This second automatic alignment uses the Z alignment detecting optical system 85 (85a and 85b). During the second automatic alignment, the CPU 91 lights the light source 86 to continuously project detection light from the light projecting optical system 85a to the cornea Ec. The light source 86 may be lighted up in advance. This continuous light projection may be always-on light projection or intermittent light projection. The light projection control of detection light is not limited to lighting control of the light source 86. For instance, a light-blocking drive part (e.g., AOM) may be provided in the light projecting optical system 85a. In this case, the CPU 91 controls the light-blocking part to control projection of the detection light.

Corneal reflection light of the detection light is detected by the detector 89 of the detecting optical system 85b. The CPU 91 controls the actuator 5 based on a signal output from the detector 89 to thereby move the photographing part 1 in the Z direction. For instance, the CPU 91 detects a peak P corresponding to the reflection light from the corneal epithelium in a waveform indicating an intensity distribution of the corneal reflection light in the depth direction, based on the intensity distribution represented by the signal output from the detector 89 (see FIG. 6). The actuator 5 is driven so that a position Pz of the epithelium peak on the detector 89 comes to the position of a predetermined pixel (e.g., the position of a center pixel). In the photographing apparatus 100, accordingly, focus of the cornea photographing optical system 10 is set on or near the corneal epithelium. When the alignment state in the X-, Y-, and Z-directions satisfies an alignment completion condition, the CPU 91 terminates the alignment processing (S4) and turns off the alignment light source (S5).

Figure 6:
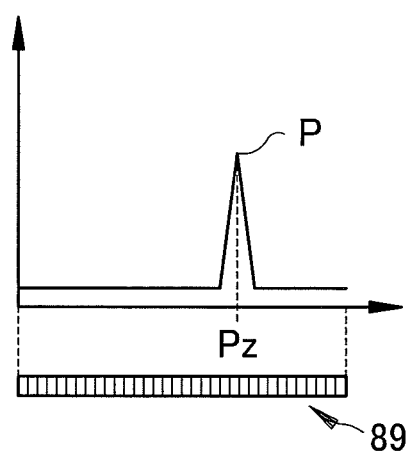
FIG. 6 is a graph showing an epithelial peak detected on a detector.

The CPU 91 may detect the peak corresponding to reflection light beam from a corneal endothelium in a waveform representing the intensity of the reflection light beam from the cornea Ec per depth of the cornea Ec, based on the intensity distribution output from the detector 89 (see FIG. 6). The actuator 5 may also be driven to bring the position of the endothelial peak on the detector 89 to a predetermined pixel (e.g., the position of a center pixel) on the detector 89. In the photographing apparatus 100, accordingly, focus of the cornea photographing optical system 10 is set on or near the corneal endothelium.

The CPU 91 then executes the observation and photographing processing (S6). In this observation and photographing processing (S6), displaying an observation image of the corneal endothelium (a live image of endothelial image in the present embodiment) and acquiring and storing (capturing) of the photographed image are performed. When the observation and photographing processing (S6) is carried out, the endothelium observation screen 300 is displayed on the monitor 97 (see FIG. 7). The live image of endothelial image is displayed in an endothelium window 301 on the endothelium observation screen 300. The endothelium observation screen 300 displays thereon corneal reflection light information together with the endothelial image. The corneal reflection light information relates to the intensity of corneal reflection light received by the detector 89 per corneal depth (i.e., an intensity distribution of corneal reflection light in the depth direction (Z direction), including at least an intensity distribution corresponding to the reflection light from the corneal endothelium). Subsequent to the second automatic alignment, the CPU 91 controls the light projecting optical system 85a to continuously project the detection light.

Figure 7:
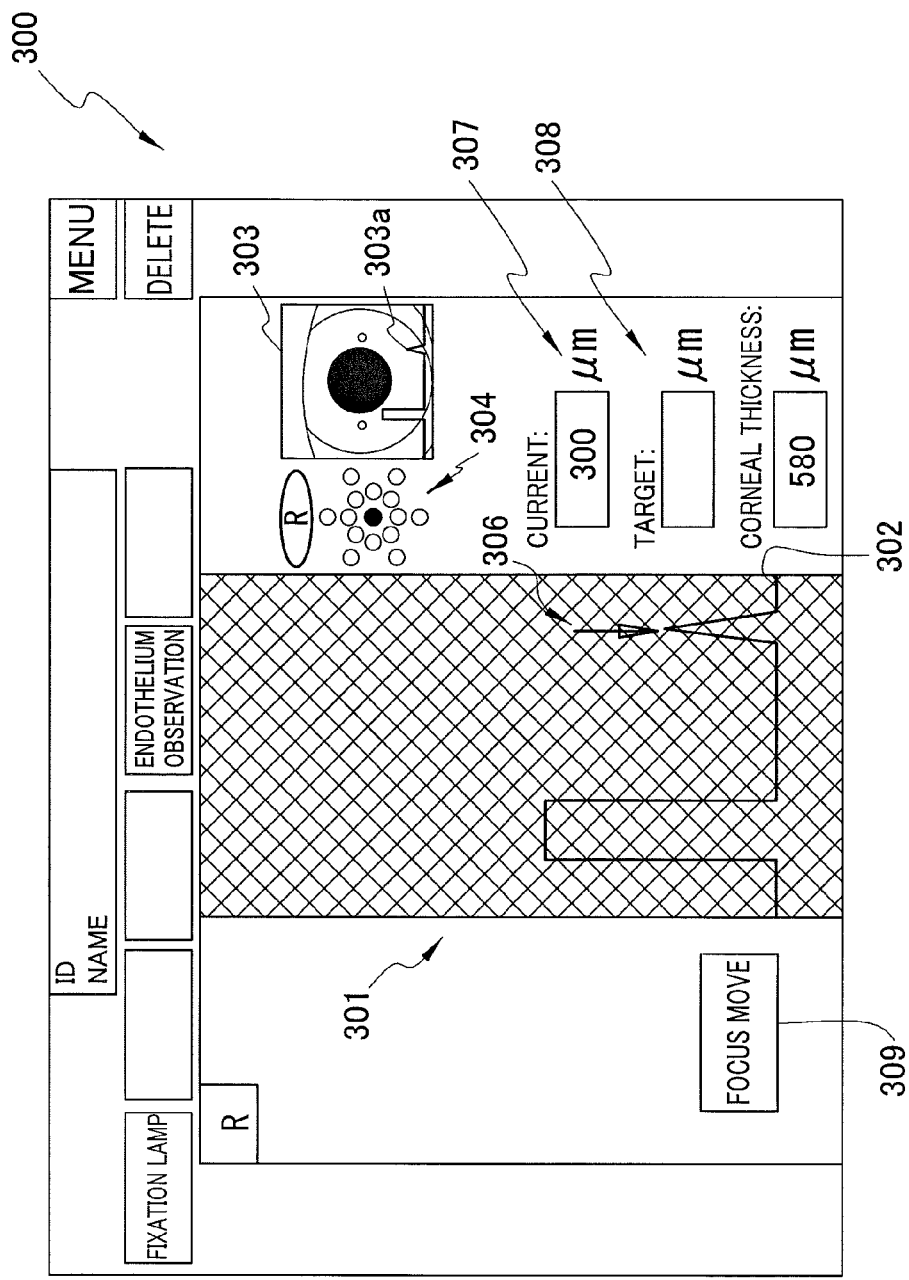
FIG. 7 is a schematic diagram showing one example of an endothelium observation screen.

In the present embodiment, the intensity distribution of corneal reflection light in the depth direction is shown as a waveform in a waveform graph 302. In a case of displaying the intensity distribution as a waveform, a raw signal may be displayed or a processed signal (e.g., a signal generated by smoothing processing, amplitude emphasizing processing, etc.) may be displayed. Since the detection light is strongly reflected by the epithelium and the endothelium of the cornea Ec, as shown in FIG. 7, the information indicating that strong reflection is obtained at two locations is obtained as the corneal reflection light information. In this case, for example, the waveform graph 302 shows a waveform having two peaks, that is, a peak indicating reflection from the epithelium (i.e., epithelium peak) and a peak indicating reflection from the endothelium (i.e., endothelial peak) (see FIG. 7). However, the corneal reflection light is condensed most preferably at a predetermined pixel of the detector 89 (a center pixel in the present embodiment) and the corneal reflection light is difficult to be condensed at a pixel located in a position more away from the predetermined pixel. Thus, as compared with a case where the reflection light from the endothelium enters the predetermined pixel or another pixel located near it, as the reflection light from the endothelium enters in a pixel located more away from the predetermined pixel, a detection signal of the reflection light from the endothelium is lower in intensity. Accordingly, when the reflection light from the endothelium enters the pixel located greatly away from the predetermined pixel, an endothelial peak may be not formed. Regarding the waveform graph 302 in FIG. 7, a left side in the drawing sheet corresponds to an apparatus side and a right side corresponds to a fundus side.

When the focus position is displaced, the waveform in the waveform graph 302 is shifted in a right-and-left direction on the screen. In FIG. 7, when the focus position is moved to the fundus side, the waveform shifts to the left on the drawing sheet of FIG. 7, while when the focus position is moved to the corneal epithelium side, the waveform is shifted to the right on the drawing sheet of FIG. 7. In the present embodiment, the focus position of the cornea photographing optical system 10 on the waveform graph 302 is set at the center of the waveform graph 302 in the right-and-left direction (that is, the center position of the endothelium window 301 in the right-and-left direction in FIG. 7). In the present embodiment, therefore, an examiner can recognize the focus position with reference to the position of the waveform peak with respect to the center position of the waveform graph 302 in the right-and-left direction. In FIG. 7, the corneal reflection light information (waveform graph 302) is displayed to be superimposed on the endothelial image. However, the corneal reflection light information has only to be displayed simultaneously with the endothelial image and is not limited to the display example in the present embodiment.

In the present embodiment, an anterior segment window 303 is placed in the endothelium observation screen 300. The CPU 91 causes the anterior segment window 303 to display thereon a live image of the anterior segment image generated in the image processing IC 95. The corneal reflection light information (e.g., a waveform graph 303a) may be displayed in the anterior segment window.

On the endothelium observation screen 300, a fixation position graphic 304 is displayed. This fixation position graphic 304 represents the positions of the lighted fixation lamps 71 seen from the examinee's eye E. The fixation position graphic 304 enables the examiner to easily recognize the photographing position of the endothelial image around the corneal center.

Figure 8A:
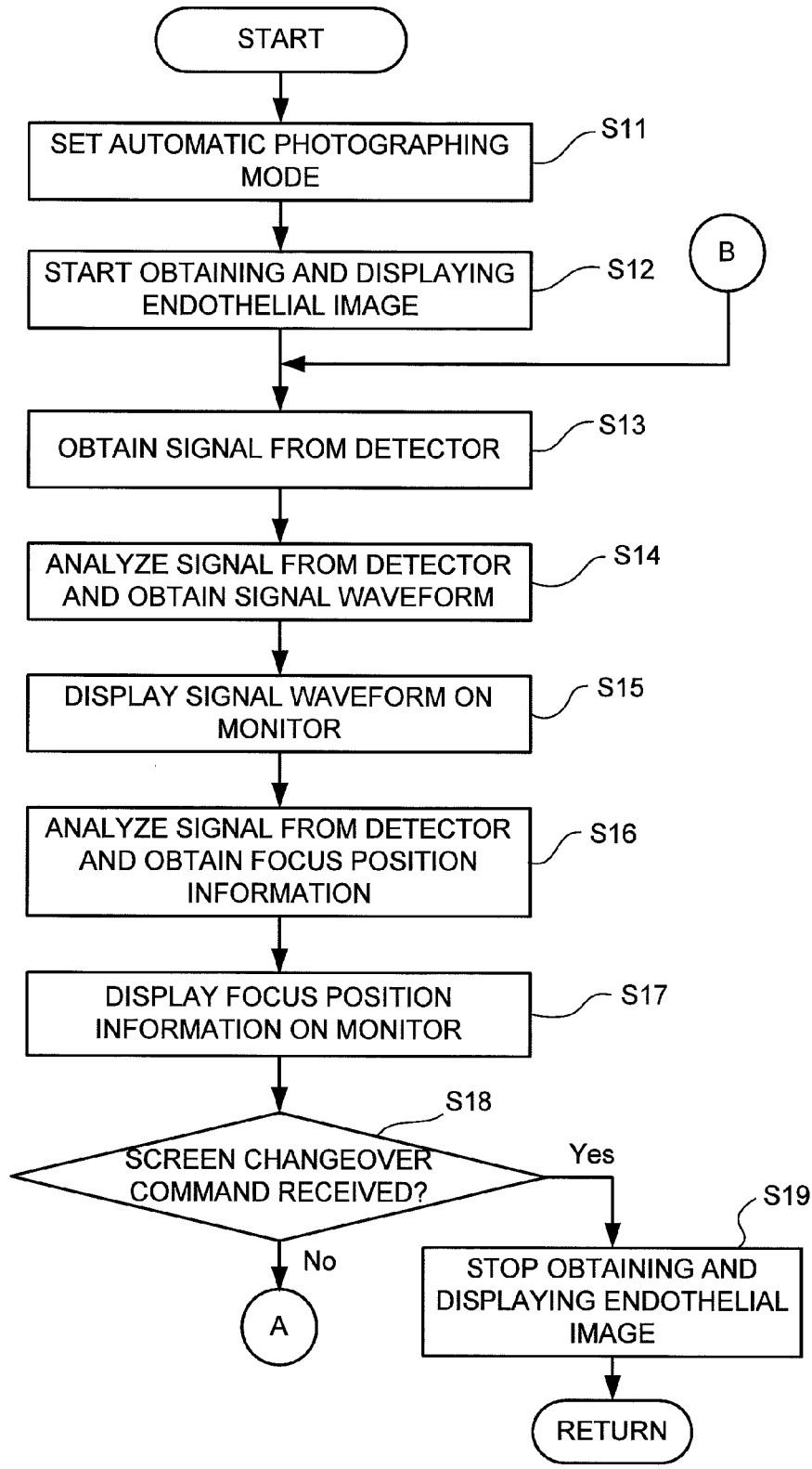
FIG. 8A is a first half of a flowchart showing observation and photographing processing to be executed in the main processing.
Figure 8B:
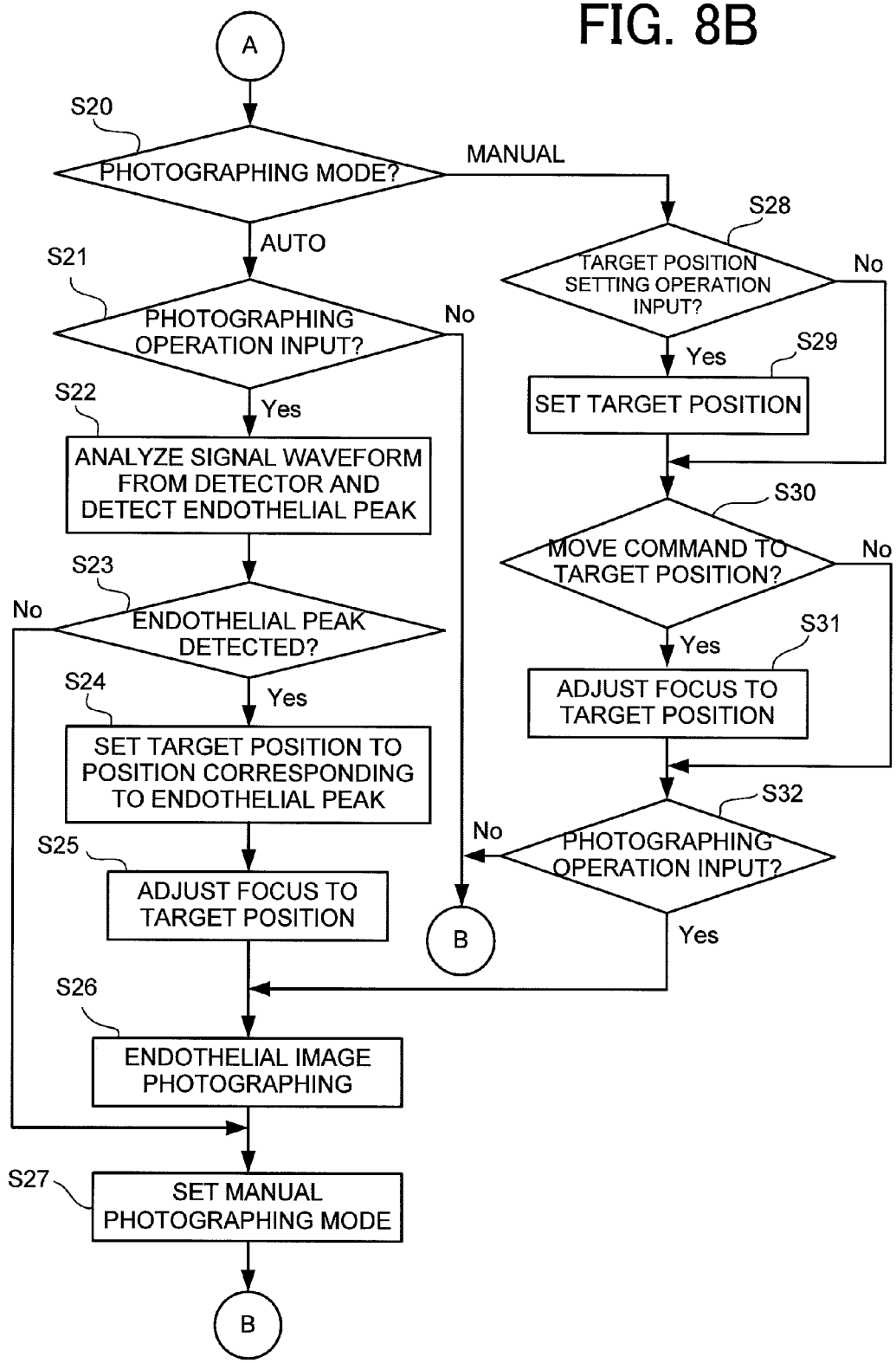
FIG. 8B is a second half of the flowchart showing the observation and photographing processing.

Herein, referring to flowcharts in FIGS. 8A and 8B, one example of the observation and photographing processing (S6) will be explained more concretely. In the observation and photographing processing (S6), firstly, a photographing mode in the controller 90 is set to an automatic photographing mode (S11).

<Automatic Photographing Mode>

When the automatic photographing mode is established, the CPU 91 controls driving of the actuator 5 based on the intensity distribution (or a signal) output from the detector 89 to automatically adjust the focus position of the cornea photographing optical system 10 to the corneal epithelium or endothelium. In the automatic photographing mode in the present embodiment, photographing and storing of the endothelial image are also automatically performed. In the present embodiment, as the photographing mode in the controller 90, a manual photographing mode may be set as well as the automatic photographing mode. In the manual photographing mode, the details of which will be mentioned later, the focus position of the cornea photographing optical system 10 is adjusted according to a command from the examiner.

After setting the automatic photographing mode, the CPU 91 gives the image processing IC 95 a command to start creating the endothelial image and displaying this image on the monitor 97 (S12). As a result of this command, a live image of the endothelial image is displayed in the endothelium window 301.

The CPU 91 then acquires a signal from the detector 89 (S13). When this signal is processed, a waveform representing an intensity distribution of corneal reflection light in the depth direction (that is, the Z direction and the back-and-forth direction) is obtained (S14). The waveform obtained by the processing in S14 is displayed as the waveform graph 302 on the monitor 97 (S15).

Further, the CPU 91 makes a determination processing on an alignment signal output from the detector 89 to obtain the focus position information representing the focus position of the cornea photographing optical system 10 (S17). In the present embodiment, the focus position information with respect to the epithelium is obtained. The focus position information with respect to the epithelium can be obtained as a value corresponding (proportional) to a difference between the epithelium peak position in the waveform graph 302 and the focus position (that is, the center of the waveform graph 302 in the right-and-left direction). Needless to say, focus position information with respect to endothelium may be obtained as well as the focus position information with respect to epithelium.

The CPU 91 subsequently displays the focus position information obtained by the processing in S16 on the monitor 97 (S17). The focus position information may be indicated by graphic or numerical value. For instance, in the present embodiment, the distance from the corneal epithelium to a real focus position is indicated by numerical value in a text box 307.

Successively, the CPU 91 determines whether or not a command to change over from the endothelium observation screen 300 to another (S18). This screen changeover command is given by operation of the operation input unit 96 by the examiner. For instance, the command may be input when a changeover button for a confirmation and analysis screen on the endothelium observation screen 300 in FIG. 7 is pressed on a touch panel. In this case, the display on the monitor 97 is changed over to a confirmation screen 400 mentioned later. If it is determined that the screen changeover command has been input (S18: Yes), the CPU 91 stops obtaining and displaying of the endothelial image (S19). Thereafter, the CPU 91 returns to the main processing and executes the processing in S7.

On the other hand, if the screen changeover command has not been input (S18: No), a photographing mode currently set is determined (S20). Since the automatic photographing mode is initially set in the processing in S11 (S20: Auto), the processing proceeds to S21. In the processing in S21, it is determined whether or not a photographing operation has been input by the examiner (S21). In the photographing apparatus 100, as described above, the photographing operation is input by operation of the switch 6b. If it is determined that the photographing operation has not been input (S21: No), the processing is returned to S13 and the processings in S13 to S21 are repeatedly executed. In the present embodiment, at that time, a live image of anterior segment image is displayed in the anterior segment window 303 of the endothelium observation screen 300. After confirming on the anterior segment window 303 that fixation of the examinee's eye E is properly performed, the examiner can photograph (capture) the endothelial image. According to the photographing apparatus 100 in the present embodiment, it is easy to photograph the endothelial image at appropriate timing at which fixation is made stable.

If the photographing operation has been input (S21: Yes), on the other hand, the CPU 91 analyzes the waveform of the alignment signal and performs the detection processing of the endothelial peak (S22). As a result of the processing in S22, it is determined whether or not the endothelial peak is detected (S23). When the endothelial peak is detected (S23: Yes), the position of the endothelial peak is set as a target position (S24). The CPU 91 detects a deviation amount (a displacement amount) between a current focus position and the endothelial peak detection position in the waveform graph 302 and starts driving of the actuator 5 according to the detected deviation amount (S25). While the focus position is being moved, the CPU 91 may continue to perform automatic alignment in the X- and Y-directions (that is, the above-described automatic alignment utilizing the anterior segment image).

After moving the focus position to the target position, the CPU 91 executes the endothelial image photographing processing (S26). In the endothelial image photographing processing (S26), the CPU 91 photographs the endothelial image. This photographed image is stored in the HDD 94. The present embodiment is explained on the assumption that a sequence of photographing operations is performed without changing a fixation position (for example, while the fixation lamps 71 continue to light up) for convenience of explanation. However, needless to say, photographing may be carried out by changing the fixation position from one to another among a plurality of fixation positions to perform peripheral photographing peripheral areas of the corneal apex.

The endothelial image photographing processing (S26) in the present embodiment obtains an endothelial image at each of a plurality of surrounding focus positions around the target position based on signals from the detector 89 by driving the actuator 5 to each of the focus positions. Further, a plurality of obtained endothelial images that are photographed at the same fixation position are each analyzed and, from among these, one endothelial image is selected in which most endothelial cells are detected.

In the present embodiment, only the selected image is stored in the HDD 94. Accordingly, the selected image is utilized as an image to be displayed later on the confirmation and analysis screen 400 and others (see FIG. 9). The present embodiment is explained assuming that only the selected image is displayed and stored, but is not necessarily limited thereto. For example, the selected image may be set as a typical image representing a plurality of images photographed at a time. In this case, each image is stored in the HDD 94 and displayed on the confirmation and analysis screen 400 and others. As an alternative, the typical image may be an image to be preferentially displayed from among a plurality of images photographed at a time and also may be utilized as an image on which thumbnails are created corresponding to the plurality of images.

In the present embodiment, photographing of the target position and its surrounding positions in the processing in S26 is explained about the case of starting photographing after setting the focus at the target position, but it is not limited thereto. For instance, photographing may be started from when the focus position comes close to a photographing range around the target position. Further, the endothelial image photographing processing (S26) may be a processing of performing photographing only at the focus target position. While photographing is performed at a plurality of focus positions, the CPU 91 may carry out automatic alignment in the X- and Y-directions.

In the endothelial image photographing processing (S26) in the present embodiment, an anterior segment image obtained at the same time (including nearly the same time) as the endothelial image, waveform information on the signal from the detector 89, and focus position information on the focus position of the cornea photographing optical system 10 during photographing of endothelial image are stored in the HDD 94 in association with the obtained endothelial image.

After completion of the endothelial image photographing processing (S26), the CPU 91 changes over the photographing mode of the apparatus to the manual photographing mode (S27). After setting the photographing mode to the manual photographing mode, the CPU 91 returns to S13 and continues the processings therefrom.

Next, returning to the processing in S23 in which the photographing operation has been input in the automatic photographing mode, a case where the endothelial peak is not detected (S23: No) will be explained. In this case, it is not possible to set the focus target position to the endothelial peak. In the present embodiment, therefore, when a plurality of peaks are not detected in a waveform of the signal from the detector 89 (S23: No), the CPU 91 changes the photographing mode from the automatic photographing mode to the manual photographing mode (S27). In this case, accordingly, the focus position of the cornea photographing optical system 10 is adjusted according to a command from the examiner. As the case where no endothelial peak is detected, for example, there are conceived a case where reflection light from the endothelium enters a pixel located in a position away from a predetermined pixel of the detector 89, a case where a cornea has opacity or the like, and other cases. Further, at that time, the information indicating transition to the manual photographing mode or the information indicating the occurrence of photographing error in the automatic mode may be displayed on the monitor 97. In this case, the examiner can promptly start to operate the apparatus in the manual photographing mode by confirming or checking the information displayed on the monitor 97.

<Manual Photographing Mode>

Returning to S20, subsequently, the operations in the manual photographing mode will be explained. In the present embodiment, in the manual photographing mode, the examiner can manually adjust focus by manipulating the joystick 6. As an alternative, when the focus target position is input by the examiner with the operation input unit 96, the photographing apparatus 100 can adjust the focus to the target position (hereinafter, referred to as semi-automatic focus).

In the processing in S20, when it is determined that the manual photographing mode is set as the photographing mode (S20: Manual), the processing in S28 is carried out. In this processing S28, the CPU 91 determines whether or not an operation of setting the target position for semi-automatic focus has been input (S28). This target position setting operation is performed through the operation input unit 96. In the present embodiment, the setting operation is input by operation input in relation to the waveform graph 302. For example, the setting operation may be an operation of designating the position on the waveform graph 302 by use of a pointing device and others. As another example, the setting operation may be an operation of inputting a distance from the corneal epithelium to the target focus position on the text box 308 by use of a numerical keypad or the like.

When the target position setting operation has been input (S28: Yes), the target position is set to a position based on the setting operation (S29). The set target position is stored in the RAM 93. At that time, the target position information on the set target position for semi-automatic focus may be displayed on the endothelium observation screen 300. For example, the target position information may be indicated by graphic or character such as numerical value. In FIG. 7, in the waveform graph 302, a portion corresponding to the target position is emphasized (more concretely, a mark 306 is arranged on the waveform graph 302) to show the target position information. The distance from the corneal epithelium to the target focus position is also indicated by numerical value. After setting the target position, the CPU 91 executes the processing in S30. On the other hand, in the processing in S28, when it is determined that the target position setting operation has not been input (S28: No), the CPU 91 skips the processing in S29 and executes the processing in S30.

In the processing in S30, the CPU 91 determines whether or not a command to move to the target position for semi-automatic focus has been input (S30). This move command to the target position is input by the examiner through the operation input unit 96. The move command may be input for example by operation of a focus move button 309 on the endothelium observation screen 300 by use of a pointing device or the like.

When the move command to the target position has been input (S30: Yes), the CPU 91 controls driving of the actuator 5 to move the focus position of the anterior segment photographing optical system 10 to the target position (S31). The CPU 91 detects a deviation amount (a displacement amount) between a current focus position and the target position and drives the actuator 5 based on the detected deviation amount. For instance, the photographing part 1 is moved based on a drive amount corresponding to the deviation amount between the current focus potion (the center of the endothelium window 301) determined in advance on the waveform graph 302 and the target position (i.e., the position at which the mark 306 is arranged on the waveform graph 302). In a case where the focus target position is determined with reference to the epithelial position, for example, it may be arranged to detect a difference between the deviation amount of a current epithelial position from the previously set focus position (the center position of the waveform graph 302 in the right-and-left direction in the present embodiment) and the deviation amount between the focus target position and the epithelial position and then drive the actuator 5 according to the detected difference. In the control of the actuator during the above-described automatic focus, the positional information based on the epithelium may be utilized.

While the focus position is being moved, the CPU 91 may perform automatic alignment in the X- and Y-directions. After the focus of the cornea photographing optical system 10 is set to the target position, the CPU 91 executes the processing in S32. In the processing in S30, on the other hand, when it is determined that the move command to the target position has not been input (S30: No), the CPU 91 skips the processing in S31 and executes the processing in S32.

In the processing in S32, the CPU 91 determines whether or not the photographing operation has been input (S32). The processing in S32 is the same as that in S21 mentioned above and thus a detailed explanation of the determination method is omitted. When it is determined that the photographing operation has not been input (S32: No), the processing returns to S13. Accordingly, until the photographing operation is input, the processings in S13 to S20 and S28 to S31 are repeatedly executed. Accordingly, the examiner can adjust the focus by operation of the joystick 6 or by use of the semi-automatic focus while confirming or observing the endothelial image, the waveform graph 302, the focus position information, the anterior segment image, and others, displayed on real time on the monitor 97.

In the processing in S32, on the other hand, when it is determined that the photographing operation has been input (S32: Yes), the endothelial image photographing processing (S26) is executed. In the manual photographing mode in the present embodiment, accordingly, photographing of the endothelial image is performed at the focus position at which the photographing operation has been performed and at a plurality of surrounding focus positions.

Returning to FIG. 5, the main processing is continued. After termination of the observation and photographing processing (S6), in the present embodiment, the screen of the monitor 97 is changed over to the confirmation screen 400 (S7). The confirmation screen 400 is a screen for displaying the endothelial image photographed in the observation and photographing processing (S6) and stored in the HDD 94.

<Confirmation Screen Display>

Figure 9:
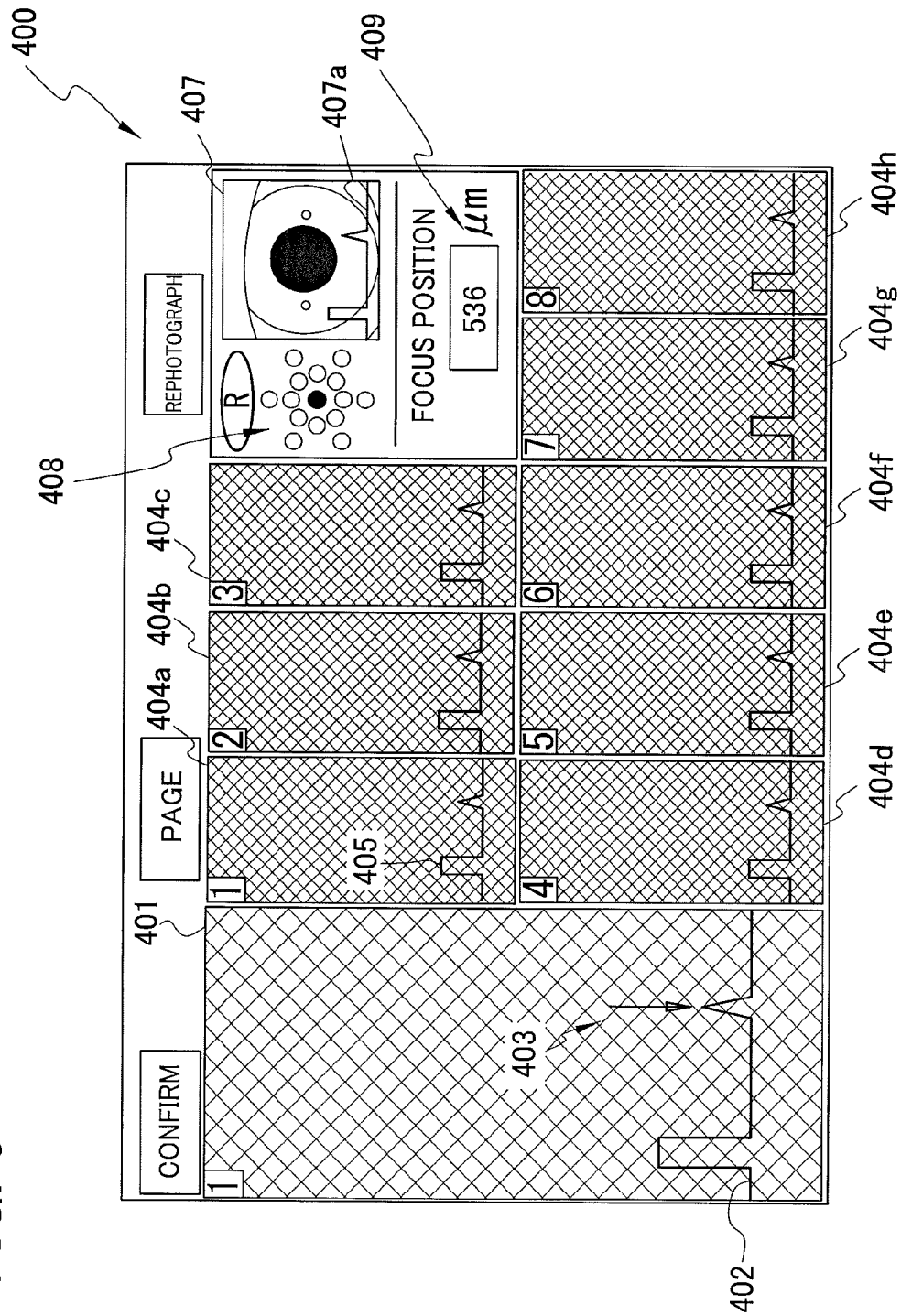
FIG. 9 is a schematic diagram showing one example of a confirmation screen.

Herein, one example of the confirmation screen 400 is explained, referring to FIG. 9. In a zoom window 401 of the confirmation screen 400, the endothelial image retrieved from the HDD 94 is displayed. On the confirmation screen 400, a plurality of thumbnails 404a to 404h are displayed. These thumbnails 404a to 404h are thumbnails of the endothelial images stored in the HDD 94. One endothelial image displayed in the thumbnail selected by the examiner by operation of the pointing device or the like is displayed in the zoom window 401. In the present embodiment, the corneal reflection light information (a waveform graph 402 of an alignment signal of the endothelial image in FIG. 9) is displayed along with the endothelial image displayed in the zoom window 401. The examiner can refer to the waveform graph 402 displayed on the confirmation screen 400 for the focus position during re-photographing.

Furthermore, the focus position information obtained during photographing of the endothelial image is displayed. In FIG. 9, the focus position information is indicated by numerical value (e.g., a distance from the corneal epithelium to the focus position). The focus position information may be used as a reference during re-photographing of endothelial image. For example, the examiner can determine the focus position during re-photographing by using the focus position information on the endothelial image photographed well.

On the conformation screen 400, the anterior segment window 407 shows therein the anterior segment image stored in the HDD 94 in association with the endothelial image displayed in the zoom window 401. The anterior segment image displayed in the anterior segment window 407 is an image photographed at the same time (or at nearly the same time) with the endothelial image displayed in the zoom window 401. Accordingly, for example, based on the anterior segment image in the anterior segment window 407, the examiner can confirm whether or not photographing of the endothelial image has been appropriately performed.

The fixation position related to the endothelial image displayed in the zoom window 401 is presented by a fixation position graphic 408. This enables the examiner to easily confirm the fixation position determined at the time of previous photographing and photograph the same portion during re-photographing as that during previous photographing.

As shown in FIG. 9, in the thumbnails 404a to 404h, a waveform graph 405 of signal from the detector 89 and others may also be displayed.

The present disclosure is not limited to the above-described examples and may be embodied in other specific forms without departing from the essential characteristics thereof.

For example, the above-described embodiment is explained in the case where the focus position information is indicated by numerical values, but it is not limited thereto and it may be displayed by graphics. For instance, it may be arranged to emphasize the focus position on the waveform graph 302 by using a mark at the focus position (that is, the center position of the waveform graph 302 in the right-and-left direction).

What is claimed is:

1. A corneal endothelial cell photographing apparatus for photographing endothelial cells of a cornea of an examinee's eye, comprising:
   a cornea photographing optical system including an imaging device that projects light from a photographing light source toward the cornea of the examinee's eye and photographs the corneal endothelial cells of the examinee's eye through the imaging device;
   a light projecting optical system that projects detection light in a first oblique direction to the cornea of the examinee's eye to detect a focus state of the cornea photographing optical system with respect to the cornea of the examinee's eye;
   a detecting optical system including a detector in which a plurality of pixels are arranged, the detecting optical system receiving, through the detector, in a second oblique direction opposite to the first oblique direction, corneal reflection light resulting from the detection light and including reflection light reflected from the corneal endothelium, and detecting an intensity distribution of the corneal reflection light in a depth direction of the cornea; and a controller that:
  causes a monitor to display the intensity distribution of the corneal reflection light detected in the depth direction of the cornea simultaneously with the corneal endothelial cell image based on output from the detector, the depth direction being a direction of thickness from back to front of the cornea; and
  causes the monitor to display a mark on the intensity distribution, the mark indicating a focus position of the corneal photographing optical system.

2. The corneal endothelial cell photographing apparatus according to claim 1, wherein the controller:
  continuously projects light from the photographing light source to the cornea of the examinee's eye; and
  simultaneously causes the monitor to display a live image of the corneal endothelial cell image of the examinee's eye and the intensity distribution obtained in real time on the monitor while the light from the photographing light source is continuously projected.

3. The corneal endothelial cell photographing apparatus according to claim 1, further comprising:
  an anterior segment observing optical system including a second imaging device different from the imaging device and that photographs an anterior segment image of the examinee's eye by use of the second imaging device and allows observation of the anterior segment image from front,
  wherein the controller causes the monitor to simultaneously display the intensity distribution and the corneal endothelial cell image and an image of the anterior segment image photographed by the anterior segment observing optical system on the monitor.

4. The corneal endothelial cell photographing apparatus according to claim 1, wherein the controller:
  stores the intensity distribution output from the detector at the same time when the corneal endothelial cell image is photographed, in a storage unit in association with the corneal endothelial cell image; and
  causes the corneal endothelial cell image to be retrieved from the storage unit, causes the monitor to display the corneal endothelial cell image on a monitor, and causes the monitor to display the intensity distribution corresponding to the corneal endothelial cell image, in combination with the corneal endothelial cell image.

5. The corneal endothelial cell photographing apparatus according to claim 1, further comprising:
  an actuator that moves a housing accommodating the photographing optical system, the light projecting optical system, and the detecting optical system in at least a back-and-forth direction,
  wherein the controller controls the actuator based on a signal from the detector.

6. The corneal endothelial cell photographing apparatus according to claim 5, wherein the controller:
  analyzes the intensity distribution output from the detector to detect a peak in the intensity distribution; and
  changes from a first mode of controlling the actuator based on the detected peak position to automatically move the housing to a second mode of moving the housing according to operation of an examiner after performing control in the first mode and displaying the intensity distribution on the monitor.

7. The corneal endothelial cell photographing apparatus according to claim 1, wherein the controller causes the monitor to display the intensity distribution in a graph on the monitor.

8. The corneal endothelial cell photographing apparatus according to claim 5, wherein the controller:
  causes the monitor to display the intensity distribution in a graph on the monitor; and
  sets a target position of focus based on an operation input from an examiner with respect to the graph displayed on the monitor, and drives the actuator to bring the focus of the cornea photographing optical system to the target position.

9. The corneal endothelial cell photographing apparatus according to claim 6, wherein the controller stores a corneal endothelial cell image of the examinee's eye in a storage unit based on a signal output from the imaging device in response to a photographing start signal from a user interface.

10. The corneal endothelial cell photographing apparatus according to claim 8, wherein the controller stores a corneal endothelial cell image of the examinee's eye in a storage unit based on a signal output from the imaging device in response to a photographing start signal from a user interface.

11. The corneal endothelial cell photographing apparatus according to claim 5, wherein the controller:
  analyzes the intensity distribution output from the detector to detect an epithelial position of the cornea of the examinee's eye; and
  sets a target position of focus based on an operation input from an examiner in correspondence with a deviation amount from an epithelial position, and drives the actuator to bring the focus of the cornea photographing optical system to the target position.

12. The corneal endothelial cell photographing apparatus according to claim 11, wherein the controller stores, in a storage unit, epithelial position data corresponding to the epithelial position detected by the controller or corresponding to the operation input date, in association with the corneal endothelial cell image, at the same time when the corneal endothelial cell image is photographed.

13. A corneal endothelial cell photographing apparatus for photographing endothelial cells of a cornea of an examinee's eye, comprising:
  a cornea photographing optical system including an imaging device that projects light from a photographing light source toward the cornea of the examinee's eye and photographs the corneal endothelial cells of the examinee's eye through the imaging device;
  a light projecting optical system that projects detection light in a first oblique direction to the cornea of the examinee's eye to detect a focus state of the cornea photographing optical system with respect to the cornea of the examinee's eye;
  a detecting optical system including a detector in which a plurality of pixels are arranged, the detecting optical system receiving, through the detector, in a second oblique direction opposite to the first oblique direction, corneal reflection light resulting from the detection light and including reflection light reflected from the corneal endothelium, and detecting an intensity distribution of the corneal reflection light in a depth direction of the cornea;
  an actuator that moves a housing accommodating the photographing optical system, the light projecting optical system, and the detecting optical system in at least a back-and-forth direction; and
  a controller that:
    causes a monitor to display the intensity distribution of the corneal reflection light detected in the depth direction of the cornea based on output from the detector, the depth direction being a direction of thickness from back to front of the cornea;

causes the monitor to display the intensity distribution in a graph on the monitor;

sets a target position of focus based on an operation input from an examiner with respect to the graph displayed on the monitor, and drives the actuator to bring the focus of the cornea photographing optical system to the target position; and controls the actuator based on a signal from the detector, wherein the controller causes the monitor to display the intensity distribution in a graph on the monitor, and wherein the controller causes the monitor to display a mark on the intensity distribution, the mark indicating a focus position of the corneal photographing optical system.

14. The corneal endothelial cell photographing apparatus according to claim 13, wherein the controller causes the monitor to display the intensity distribution output from the detector simultaneously with the corneal endothelial cell image.

15. The corneal endothelial cell photographing apparatus according to claim 13, wherein the controller:

continuously projects light from the photographing light source to the cornea of the examinee's eye; and simultaneously causes the monitor to display a live image of the corneal endothelial cell image of the examinee's eye and the intensity distribution obtained in real time on the monitor while the light from the photographing light source is continuously projected.

* * * * *